United States Patent
Rosentreter et al.

(10) Patent No.: US 7,825,255 B2
(45) Date of Patent: Nov. 2, 2010

(54) ADENOSINE RECEPTOR SELECTIVE MODULATORS

(75) Inventors: Ulrich Rosentreter, Wuppertal (DE); Thomas Krämer, Wuppertal (DE); Andrea Vaupel, Riehen (CH); Walter Hübsch, Wuppertal (DE); Nicole Diedrichs, Wuppertal (DE); Thomas Krahn, Hagen (DE); Klaus Dembowsky, Boston, MA (US); Johannes-Peter Stásch, Solingen (DE)

(73) Assignee: Bayer Schering Pharma Aktiengesellschaft, Berlin (DE)

( * ) Notice: Subject to any disclaimer, the term of this patent is extended or adjusted under 35 U.S.C. 154(b) by 1974 days.

(21) Appl. No.: 10/471,079

(22) PCT Filed: Feb. 28, 2002

(86) PCT No.: PCT/EP02/02121
§ 371 (c)(1),
(2), (4) Date: Apr. 5, 2004

(87) PCT Pub. No.: WO02/070485
PCT Pub. Date: Sep. 12, 2002

(65) Prior Publication Data
US 2006/0154969 A1 Jul. 13, 2006

(30) Foreign Application Priority Data
Mar. 7, 2001 (DE) .................. 101 10 754

(51) Int. Cl.
C07D 401/00 (2006.01)
C07D 409/00 (2006.01)
C07D 405/00 (2006.01)
C07D 213/84 (2006.01)
C07D 213/72 (2006.01)

(52) U.S. Cl. .............. 546/268.1; 546/274.4; 546/278.4; 546/280.4; 546/283.4; 546/287; 546/307

(58) Field of Classification Search .............. 546/268.1, 546/273, 278.4, 274.4, 280.4, 283.4, 287, 546/307
See application file for complete search history.

(56) References Cited

U.S. PATENT DOCUMENTS 7,045,632 B2 * 5/2006 Small .................. 546/264
7,078,417 B2 * 7/2006 Rosentreter et al. ......... 514/333
7,109,218 B2 * 9/2006 Rosentreter et al. ......... 514/332
7,135,486 B1 * 11/2006 Rosentreter et al. ......... 514/344

FOREIGN PATENT DOCUMENTS

WO 0125210 4/2001
WO 0162233 8/2001

OTHER PUBLICATIONS

Kambe et al., "Synthetic Studies Using α,β-Unsaturated Nitriles: Facile Synthesis of Pyridine Derivatives", Synthesis, vol. 7, pp. 531-533 (1981).*
Olah, M.E. et al., "Cloning expression, and characterization of the unique bovine A1 adenosine receptor. Studies on the ligand binding site by site-directed mutagenesis." J. Biol. Chem. 267, 10764-10770, (1992).
Klotz, K.N. et al., "Comparative pharmacology of human adenosine receptor subtypes—characterization of stably transfected receptors in CHO Cells." Naunyn Schmiedebergs Arch. Pharmacol. 357, 1-9, (1998).
Poulsen, S.A. et al., "Adeonosine Receptors: New Opportunities for Future Drugs". Bioorganic and Medicinal Chem, 6, 619-641, (1998).
Broadley, K.J., "Drugs modulating adenosine receptors as potential therapeutic agents for cardiovascular diseases." Exp. Opin. Ther. Patents, 10, 1669-1692 (2000).
Jacobson, K., van Galen, P., Williams, M., "Adenosine Receptors: Pharmacology, Structure-Activity Relationships, and Therapeutic Potential", J. Med. Chem., 35(3): 407-422(1992).
Poulsen, S., Quinn, R., "Adenosine Receptors: New Opportunities for Future Drugs", Bioorganic & Med. Chem., 6: 619-641(1998).

* cited by examiner

*Primary Examiner*—Kevin Weddington
(74) *Attorney, Agent, or Firm*—Edwards Angell Palmer & Dodge LLP; Nicholas J. DiCeglie, Jr.; Ralph A. Loren

(57) ABSTRACT

The invention relates to the compounds of formula (I), to a method for producing the same and to the use thereof as medicaments.

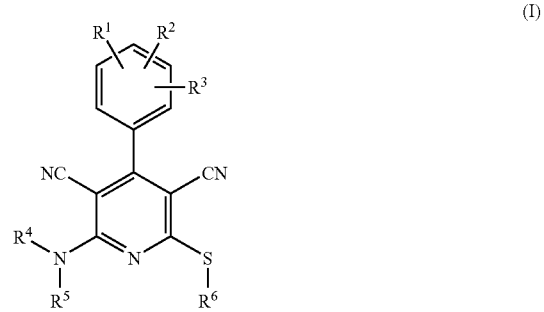

5 Claims, No Drawings

ADENOSINE RECEPTOR SELECTIVE MODULATORS

The present invention relates to substituted 2-thio-3,5-dicyano-4-aryl-6-amino-pyridines, to a process for their preparation and to their use as medicaments.

Adenosine, a nucleoside consisting of adenine and D-ribose, is an endogenous factor having cell-protective activity, in particular under cell-damaging conditions with limited oxygen and substrate supply, such as, for example, in the case of ischemia in various organs (for example heart and brain).

Adenosine is formed intracellularly as an intermediate during the degradation of adenosine-5'-monophosphate (AMP) and S-adenosylhomocysteine, but it can be released from the cell, in which case it acts as a hormone-like substance or neurotransmitter by binding to specific receptors.

Under normoxic conditions, the concentration of free adenosine in the extracellular space is very low. However, under ischemic or hypoxic conditions, the extracellular concentration of adenosine in the affected organs is increased dramatically. Thus, it is known, for example, that adenosine inhibits platelet aggregation and increases the blood supply to the coronary arteries. Furthermore, it acts on the heart rate, on the release of neurotransmitters and on lymphocyte differentiation.

The aim of these actions of adenosine is to increase the oxygen supply of the affected organs and/or to reduce the metabolism of these organs in order to adjust the metabolism of the organ to the blood supply of the organ under ischemic or hypoxic conditions.

The action of adenosine is mediated via specific receptors. To date, subtypes A1, A2a, A2b and A3 are known. The actions of these adenosine receptors are mediated intracellularly by the messenger cAMP. In the case of the binding of adenosine to the A2a or A2b receptors, the intracellular cAMP is increased via activation of the membrane-bound adenylate cyclase, whereas binding of adenosine to the A1 or A3 receptors results in a decrease of the intracellular cAMP concentration via inhibition of adenylate cyclase.

According to the invention, "adenosine-receptor-selective ligands" are substances which bind selectively to one or more subtypes of the adenosine receptors, thus either mimicking the action of adenosine (adenosine agonists) or blocking its action (adenosine antagonists).

According to their receptor selectivity, adenosine-receptor-selective ligands can be divided into different categories, for example ligands which bind selectively to the A1 or A2 receptors of adenosine and in the case of the latter also, for example, those which bind selectively to the A2a or the A2b receptors of adenosine. Also possible are adenosine receptor ligands which bind selectively to a plurality of subtypes of the adenosine receptors, for example ligands which bind selectively to the A1 and the A2, but not to the A3 receptors of adenosine.

The abovementioned receptor selectivity can be determined by the effect of the substances on cell lines which, after stable transfection with the corresponding cDNA, express the receptor subtypes in question (see the publication M. E. Olah, H. Ren, J. Ostrowski, K. A. Jacobson, G. L. Stiles, "Cloning, expression, and characterization of the unique bovine A1 adenosine receptor. Studies on the ligand binding site by, site-directed mutagenesis." in J. Biol. Chem. 267 (1992) pages 10764-10770, the disclosure of which is hereby fully incorporated by way of reference).

The effect of the substances on such cell lines can be monitored by biochemical measurement of the intracellular messenger cAMP (see the publication K. N. Klotz, J. Hessling, J. Hegler, C. Owman, B. Kull, B. B. Fredholm, M. J. Lohse, "Comparative pharmacology of human adenosine receptor subtypes—characterization of stably transfected receptors in CHO cells" in Naunyn Schmiedebergs Arch. Pharmacol. 357 (1998) pages 1-9, the disclosure of which is hereby fully incorporated by way of reference).

The "adenosine-receptor-specific" ligands known from the prior art are mainly derivatives based on natural adenosine (S.-A. Poulsen and R. J. Quinn, "Adenosine receptors: new opportunities for future drugs" in Bioorganic and Medicinal Chemistry 6 (1998) pages 619 to 641; K. J. Broadley, "Drugs modulating adenosine receptors as potential therapeutic agents for cardiovascular diseases" in Exp. Opin. Ther. Patents 10 (2000) pages 1669-1692). However, most of the adenosine ligands known from the prior art have the disadvantage that their action is not really receptor-specific, that their activity is less than that of natural adenosine or that they have only very weak activity after oral administration. Thus, owing to the aforementioned disadvantages, they are mainly used only for experimental purposes.

It is an object of the present invention to find or provide pharmacologically active substances suitable for the prophylaxis and/or treatment of various disorders, in particular disorders of the cardiovascular system (cardiovascular disorders), the substances preferably acting as adenosine-receptor-selective ligands.

The present invention relates to compounds of the formula (I)

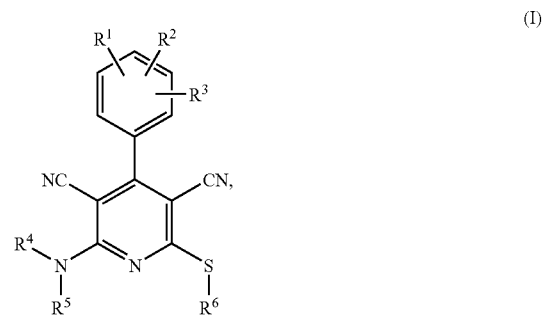

in which $R^1$, $R^2$ and $R^3$ independently of one another represent ($C_1$-$C_8$)-alkyl which may be substituted up to three times, independently of one another, by hydroxyl, ($C_1$-$C_4$)-alkoxy, ($C_3$-$C_7$)-cycloalkyl, ($C_2$-$C_4$)-alkenyl, ($C_2$-$C_4$)-alkynyl, halogen or ($C_6$-$C_{10}$)-aryloxy, ($C_6$-$C_{10}$)-aryl which may be substituted up to three times, independently of one another, by halogen, nitro, ($C_1$-$C_4$)-alkoxy, carboxyl, ($C_1$-$C_4$)-alkoxy-carbonyl or mono- or di-($C_1$-$C_4$)-alkylamino, ($C_1$-$C_8$)-alkoxy which may be substituted by hydroxyl, ($C_1$-$C_4$)-alkoxy, ($C_3$-$C_7$)-cycloalkyl, ($C_2$-$C_4$)-alkenyl, ($C_6$-$C_{10}$)-aryl, 5- or 6-membered heteroaryl having up to three heteroatoms from the group consisting of N, O and/or S, ($C_6$-$C_{10}$)-aryloxy, halogen, cyano, ($C_1$-$C_4$)-alkoxycarbonyl, amino or mono- or di-($C_1$-$C_4$)-alkylamino, hydrogen, hydroxyl, halogen, nitro, cyano, or —NH—C(O)—$R^7$, in which $R^7$ represents ($C_1$-$C_8$)-alkyl which may be substituted by hydroxyl or ($C_1$-$C_4$)-alkoxy, ($C_3$-$C_7$)-cycloalkyl or ($C_6$-$C_{10}$)-aryl which may be substituted up to three times, independently of one another, by halogen, nitro, $(C_1-C_4)$-alkoxy, carboxyl, $(C_1-C_4)$-alkoxycarbonyl or mono- or di-$(C_1-C_4)$-alkylamino, or $R^1$ and $R^2$ are attached to adjacent phenyl ring atoms and, together with the two ring carbon atoms, form a 5- to 7-membered saturated or partially unsaturated heterocycle having one or two heteroatoms from the group consisting of N, O and/or S which may be substituted by $(C_1-C_4)$-alkyl or oxo, $R^4$ represents $(C_1-C_8)$-alkyl which may be substituted by hydroxyl, —NH—CO—$R^8$, $(C_1-C_4)$-alkoxy, $(C_3-C_7)$-cycloalkyl, $(C_6-C_{10})$-aryl, 5- or 6-membered saturated or partially unsaturated heterocyclyl having up to three heteroatoms from the group consisting of N, O and/or S or 5- or 6-membered heteroaryl having up to three heteroatoms from the group consisting of N, O and/or S, or $(C_3-C_7)$-cycloalkyl which may be substituted by hydroxyl or $(C_1-C_8)$-alkyl, in which $R^8$ represents $(C_1-C_8)$-alkyl which may be substituted by hydroxyl or $(C_1-C_4)$-alkoxy, $(C_3-C_7)$-cycloalkyl or $(C_6-C_{10})$-aryl which may be substituted up to three times, independently of one another, by halogen, nitro, $(C_1-C_4)$-alkoxy, carboxyl, $(C_1-C_4)$-alkoxycarbonyl or mono- or di-$(C_1-C_4)$-alkylamino, $R^5$ represents hydrogen or $(C_1-C_4)$-alkyl which may be substituted by hydroxyl, $(C_1-C_4)$-alkoxy or $(C_3-C_7)$-cycloalkyl, or $R^4$ and $R^5$ together with the nitrogen atom to which they are attached form a 5- to 7-membered saturated or partially unsaturated heterocycle which may contain one or two further heteroatoms from the group consisting of N, O and/or S in the ring and which may be mono- to trisubstituted, independently of one another, by oxo, fluorine, chlorine, bromine, hydroxyl, $(C_1-C_6)$-alkyl or $(C_1-C_6)$-alkoxy, and $R^6$ represents $(C_3-C_7)$-cycloalkyl or $(C_1-C_8)$-alkyl, where alkyl may be substituted up to three times, independently of one another, by $(C_3-C_7)$-cycloalkyl, hydroxyl, —CO—NH—$R^9$, $(C_1-C_4)$-alkoxy, $(C_2-C_4)$-alkenyl, $(C_6-C_{10})$-aryl or 5- to 10-membered heteroaryl having up to three heteroatoms from the group consisting of N, O and/or S, where aryl and heteroaryl for their part may be substituted by halogen, $(C_1-C_4)$-alkyl, $(C_1-C_4)$-alkoxy, amino, mono- or di-$(C_1-C_4)$-alkylamino, nitro, cyano or hydroxyl, and $R^9$ represents hydrogen, $(C_1-C_8)$-alkyl which may be substituted by hydroxyl or $(C_1-C_4)$-alkoxy, $(C_3-C_7)$-cycloalkyl or $(C_6-C_{10})$-aryl which may be substituted up to three times, independently of one another, by halogen, nitro, $(C_1-C_4)$-alkoxy, carboxyl, $(C_1-C_4)$-alkoxycarbonyl or mono- or di-$(C_1-C_4)$-alkylamino, and their salts, hydrates, hydrates of the salts and solvates.

Depending on the substitution pattern, the compounds of the formula (I) can exist in stereoisomeric forms which are either like image and mirror image (enantiomers) or not like image and mirror image (diastereomers). The invention relates both to the enantiomers or diastereomers and to their respective mixtures. The racemic forms, like the diastereomers, can be separated in a known manner into the stereoisomerically uniform components. Likewise, the present invention also relates to the tautomers of the compounds of the formula (I).

Salts of the compounds of the formula (I) can be physiologically acceptable salts of the compounds according to the invention with mineral acids, carboxylic acids, or sulfonic acids. Particular preference is given, for example, to salts with hydrochloric acid, hydrobromic acid, sulfuric acid, phosphoric acid, methanesulfonic acid, ethanesulfonic acid, toluenesulfonic acid, benzenesulfonic acid, naphthalene-disulfonic acid, trifluoroacetic acid, acetic acid, propionic acid, lactic acid, tartaric acid, citric acid, fumaric acid, maleic acid or benzoic acid.

Salts which may be mentioned include salts with customary bases, such as, for example, alkali metal salts (for example sodium salts or potassium salts), alkaline earth metal salts (for example calcium salts or magnesium salts) or ammonium salts, derived from ammonia or organic amines, such as, for example, diethylamine, triethylamine, ethyldiisopropylamine, procaine, dibenzylamine, N-methyl-morpholine, dihydroabietylamine, 1-ephenamine or methylpiperidine.

According to the invention, hydrates or solvates are those forms of the compounds of the formula (I) which, in solid or liquid state, form, by hydration with water or coordination with solvent molecules, a molecule compound or a complex. Examples of hydrates are sesquihydrates, monohydrates, dihydrates or trihydrates. Likewise, the hydrates or solvates of salts of the compounds according to the invention are also suitable.

Moreover, the invention also includes prodrugs of the compounds according to the invention. According to the invention, prodrugs are forms of compounds of the formula (I) which for their part may be biologically active or inactive, but which can be converted under physiological conditions (for example metabolically or solvolytically) into the corresponding biologically active form.

In the context of the present invention, the substituents have, unless defined otherwise, the following meanings:

Halogen generally represents fluorine, chlorine, bromine or iodine. Preference is given to fluorine, chlorine or bromine. Very particularly preferred are fluorine or chlorine.

$(C_1-C_8)$-Alkyl, $(C_1-C_6)$-alkyl and $(C_1-C_4)$-alkyl generally represent a straight-chain or branched alkyl radical having 1 to 8, 1 to 6 and 1 to 4 carbon atoms, respectively. Preference is given to a straight-chain or branched alkyl radical having 1 to 6 carbon atoms. Particular preference is given to a straight-chain or branched alkyl radical having 1 to 4 carbon atoms. Examples which may be mentioned are: methyl, ethyl, n-propyl, isopropyl, n-butyl, sec-butyl, isobutyl and tert-butyl.

$(C_2-C_4$-Alkenyl generally represents a straight-chain or branched alkyl radical having 2 to 4 carbon atoms. Examples which may be mentioned are: vinyl, allyl, isopropenyl and n-but-2-en-1-yl.

$(C_2-C_4)$-Alkynyl generally represents a straight-chain or branched alkynyl radical having 2 to 4 carbon atoms. Examples which may be mentioned are: ethynyl, n-prop-2-yn-1-yl and n-but-2-yn-1-yl.

$(C_1-C_8)$-Alkoxy, $(C_1-C_6)$-alkoxy and $(C_1-C_4)$-alkoxy generally represent a straight-chain or branched alkoxy radical having 1 to 8, 1 to 6 and 1 to 4 carbon atoms, respectively. Preference is given to a straight-chain or branched alkoxy radical having 1 to 6 carbon atoms. Particular preference is given to a straight-chain or branched alkoxy radical having 1 to 4 carbon atoms. Examples which may be mentioned are: methoxy, ethoxy, n-propoxy, isopropoxy, n-butoxy, sec-butoxy, isobutoxy, tert-butoxy.

($C_1$-$C_4$)-Alkoxycarbonyl generally represents a straight-chain or branched alkoxy radical having 1 to 4 carbon atoms which is attached via a carbonyl group. Examples which may be mentioned are: methoxycarbonyl, ethoxycarbonyl, n-propoxycarbonyl, isopropoxycarbonyl and t-butoxycarbonyl.

In the context of the invention, mono- or di-($C_1$-$C_4$)-alkylamino represents an amino group having one or two identical or different straight-chain or branched alkyl substituents each having 1 to 4 carbon atoms. Examples which may be mentioned are: methylamino, ethylamino, n-propylamino, isopropylamino, t-butylamino, N,N-dimethylamino, N,N-diethylamino, N-ethyl-N-methylamino, N-methyl-N-n-propylamino, N-isopropyl-N-n-propylamino and N-t-butyl-N-methylamino.

($C_3$-$C_7$)-Cycloalkyl and ($C_3$-$C_6$)-cycloalkyl generally represent a cyclic alkyl radical having 3 to 7 and 3 to 6 carbon atoms, respectively. Preference is given to cyclic alkyl radicals having 3 to 6 carbon atoms. Examples which may be mentioned are: cyclopropyl, cyclobutyl, cyclopentyl or cyclohexyl.

($C_6$-$C_{10}$)-Aryl generally represents an aromatic radical having 6 to 10 carbon atoms. Preferred aryl radicals are phenyl and naphthyl.

($C_{6-10}$)-Aryloxy generally represents an aromatic radical as defined above which is attached via an oxygen atom.

5- to 10-membered heteroaryl having up to 3 heteroatoms from the group consisting of N, O and/or S generally represents a mono- or bicyclic, optionally benzo-fused heteroaromatic which is attached via a ring carbon atom of the heteroaromatic, if appropriate also via a ring nitrogen atom of the heteroaromatic. Examples which may be mentioned are: pyridyl, pyrimidyl, pyridazinyl, pyrazinyl, thienyl, furyl, pyrrolyl, pyrazolyl, imidazolyl, triazolyl, thiazolyl, oxazolyl, oxdiazolyl, isoxazolyl, benzofuranyl, benzothienyl or benzimidazolyl. The corresponding heteroaromatics having fewer heteroatoms, such as, for example, those having one or 2 heteroatoms from the group consisting of N, O and/or S, or those having a smaller ring size, such as, for example, 5- or 6-membered heteroaryl, are derived analogously from this definition. In general, preference is given to 5- or 6-membered aromatic heterocycles having one or 2 heteroatoms from the group consisting of N, O and/or S. Examples which may be mentioned are: pyridyl, pyrimidyl, pyridazinyl, furyl, imidazolyl or thienyl.

5- to 7-membered heterocycle generally represents a saturated or partially unsaturated, optionally benzo-fused heterocycle having up to 3 heteroatoms from the group consisting of N, O and/or S. Examples which may be mentioned are: tetrahydrofuryl, pyrrolidinyl, pyrrolinyl, dihydropyridinyl, piperidinyl, piperazinyl, morpholinyl, thiomorpholinyl, hexahydropyranyl. The corresponding heterocycles having fewer heteroatoms, such as, for example, one or 2 heteroatoms from the group consisting of N, O and/or S, or a smaller ring size, such as, for example, 5- or 6-membered heterocyclyl, are derived analogously from this definition. Preference is given to saturated heterocycles having up to 2 heteroatoms from the group consisting of N, O and/or S, in particular piperidinyl, piperazinyl, morpholinyl and pyrrolidinyl.

Preference is given to compounds of the formula (I)

in which $R^1$, $R^2$ and $R^3$ independently of one another represent hydrogen, hydroxyl, ($C_1$-$C_4$)-alkyl, trifluoromethyl, trifluoromethoxy, fluorine, chlorine, ($C_1$-$C_4$)-alkoxy which may be substituted by hydroxyl, ($C_1$-$C_4$)-alkoxy, ($C_2$-$C_4$)-alkenyl or ($C_3$-$C_6$)-cycloalkyl, —NH—C(O)—$CH_3$ or —NH—C(O)—$C_2H_5$, or $R^1$ and $R^2$ are attached to adjacent phenyl ring atoms and represent a group —O—$CH_2$—O— or —$CH_2$—$CH_2$—O—, $R^4$ represents ($C_1$-$C_6$)-alkyl which may be substituted by hydroxyl, ($C_1$-$C_4$)-alkoxy, ($C_3$-$C_6$)-cycloalkyl, —NH—C(O)—$CH_3$, phenyl, furyl, pyridyl, imidazolyl, thienyl or hexahydropyranyl, or ($C_3$-$C_6$)-cycloalkyl, $R^5$ represents hydrogen or ($C_1$-$C_4$)-alkyl which may be substituted by hydroxyl, ($C_1$-$C_4$)-alkoxy or ($C_3$-$C_6$)-cycloalkyl, or $R^4$ and $R^5$ together with the nitrogen atom to which they are attached form a 5- to 7-membered saturated or partially unsaturated heterocycle which may contain a further heteroatom from the group consisting of N, O or S in the ring and which may be mono- to trisubstituted, independently of one another, by hydroxyl, ($C_1$-$C_4$)-alkyl or ($C_1$-$C_4$)-alkoxy, and $R^6$ represents ($C_3$-$C_6$)-cycloalkyl, ($C_1$-$C_6$)-alkyl which may be substituted up to two times, independently of one another, by ($C_3$-$C_6$)-cycloalkyl, —CO—NH—$R^9$, hydroxyl, ($C_1$-$C_4$)-alkoxy, ($C_2$-$C_4$)-alkenyl, phenyl or 5- or 6-membered heteroaryl having up to three heteroatoms from the group consisting of N, O and/or S, where phenyl and heteroaryl for their part may be substituted by halogen, ($C_1$-$C_4$)-alkyl, ($C_1$-$C_4$)-alkoxy, amino, mono- or di-($C_1$-$C_4$)-alkylamino, nitro, cyano or hydroxyl, and $R^9$ represents hydrogen or ($C_1$-$C_4$)-alkyl, and their salts, hydrates, hydrates of the salts and solvates.

Particular preference is given to compounds of the formula (I)

in which $R^1$ and $R^2$ independently of one another represent hydrogen, methoxy, ethoxy, n-propoxy, isopropoxy, n-butoxy or —NH—C(O)—$CH_3$, where the alkoxy radicals for their part may be substituted by hydroxyl, methoxy, ethoxy, n-propoxy, isopropoxy, n-butoxy or cyclopropyl, or $R^1$ and $R^2$ are attached to adjacent phenyl ring atoms and represent a group —O—$CH_2$—O—, $R^3$ represents hydrogen, $R^4$ represents methyl, ethyl, n-propyl, isopropyl, where the alkyl radicals for their part may be substituted by hydroxyl, methoxy, ethoxy, n-propoxy, isopropoxy, n-butoxy, cyclopropyl, —NH—C(O)—$CH_3$, furyl, pyridyl, imidazolyl or hexahydropyranyl, or cyclopropyl, $R^5$ represents hydrogen or methyl, or $R^4$ and $R^5$ together with the nitrogen atom to which they are attached represent pyrrolidinyl, morpholinyl, piperidinyl or 4-hydroxypiperidinyl and $R^6$ represents methyl, ethyl or n-propyl, where the alkyl radicals for their part may be substituted up to two times, independently of one another, by hydroxyl, methoxy, ethoxy, n-propoxy, isopropoxy, n-butoxy, imidazolyl, nitrofuranyl, pyridyl, phenyl which for its part may in turn be substituted by cyano, nitro, methyl, ethyl, n-propyl, isopropyl, methoxy, ethoxy, n-propoxy, isopropoxy, n-butoxy or amino, —C(O)—$NH_2$ or —C(O)—NH—$CH_3$, and their salts, hydrates, hydrates of the salts and solvates.

The general or preferred radical definitions or illustrations given above can be combined with one another as desired, i.e. including combinations between the respective ranges and preferred ranges. They apply both to the end products and, correspondingly, to precursors and intermediates.

The present invention furthermore relates to a process for preparing the compounds of the formula (I), characterized in that
compounds of the formula (II)

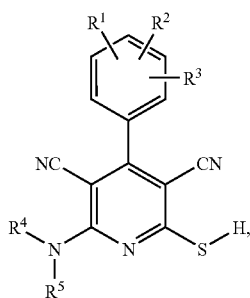

in which
$R^1$, $R^2$, $R^3$, $R^4$ and $R^5$ are as defined above
are reacted with compounds of the formula (III)

  (III)

in which
$R^6$ is as defined above and X represents a suitable leaving group in a solvent, if appropriate in the presence of a base.

The process according to the invention can be illustrated in an exemplary manner by the formula scheme below:

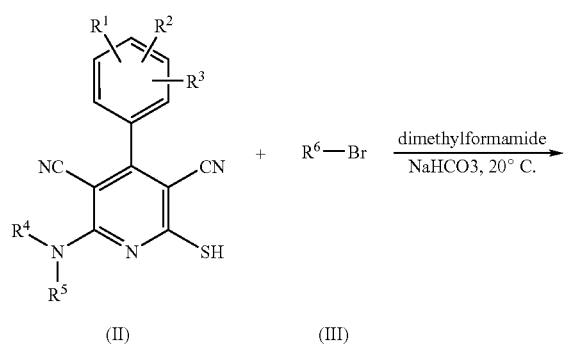

Suitable solvents for the process according to the invention are all organic solvents which are inert under the reaction conditions. These include alcohols, such as methanol, ethanol and isopropanol, ketones, such as acetone and methyl ethyl ketone, acyclic and cyclic ethers, such as diethyl ether and tetrahydrofuran, esters, such as ethyl acetate or butyl acetate, hydrocarbons, such as benzene, xylene, toluene, hexane or cyclohexane, chlorinated hydrocarbons, such as dichloromethane, chlorobenzene or dichloroethane, or other solvents, such as dimethylformamide, acetonitrile, pyridine or dimethyl sulfoxide (DMSO). Water is another suitable solvent. It is also possible to use mixtures of the solvents mentioned above. The preferred solvent is dimethylformamide.

Suitable bases are the customary inorganic or organic bases. These preferably include alkali metal hydroxides, such as, for example, sodium hydroxide or potassium hydroxide, or alkali metal carbonates, such as sodium carbonate or potassium carbonate, or alkali metal bicarbonates, such as sodium bicarbonate or potassium bicarbonate, or alkali metal alkoxides, such as sodium methoxide or potassium methoxide, sodium ethoxide or potassium ethoxide or potassium tert-butoxide, or else amides, such as sodium amide, lithium bis(trimethylsilyl)amide or lithium diisopropylamide, or organometallic compounds, such as butyllithium or phenyllithium, or else amines, such as triethylamine and pyridine. Preference is given to the alkali metal carbonates and alkali metal bicarbonates.

Suitable leaving groups X in compounds of the formula (III) are, for example: halogen, in particular chlorine, bromine or iodine, or mesylate, tosylate, triflate or 1-imidazolyl, or else a hydroxyl group activated by a Mitsunobu reaction.

The reaction is generally carried out using an equivalent amount or else an excess of compound (III), preferably in a ratio of from 1 to 4 mol of the compound (III), in particular in a ratio of from 1 to 2 mol of the compound (III), per mole of the compound (II).

Here, the base can be employed in a ratio of from 1 to 10 mol, preferably from 1 to 5 mol, in particular from 1 to 4 mol, per mole of the compounds of the formula (II).

The reaction is generally carried out in a temperature range of from −78° C. to +160° C., preferably in a range of from −78° C. to +40° C., in particular at room temperature.

The reaction can be carried out at atmospheric, elevated or reduced pressure (for example in the range from 0.5 to 5 bar). In general, the reaction is carried out at atmospheric pressure.

Compounds of the formulae (II) can be prepared by converting compounds of the formula (IV)

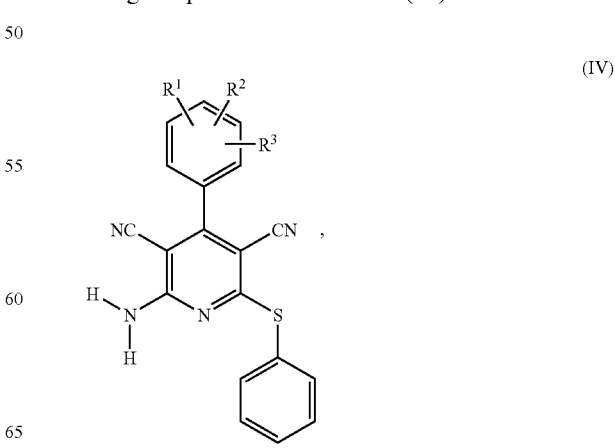

in which
R$^1$, R$^2$ and R$^3$ are as defined above
with copper(II) chloride and isoamyl nitrite in a suitable solvent into compounds of the formula (V)

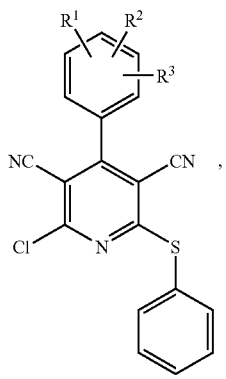

(V)

in which
R$^1$, R$^2$ and R$^3$ are as defined above,
then reacting them with compounds of the formula (VI)

R$^4$—NH—R$^5$ (VI)

in which
R$^4$ and R$^5$ are as defined above
to give compounds of the formula (VII)

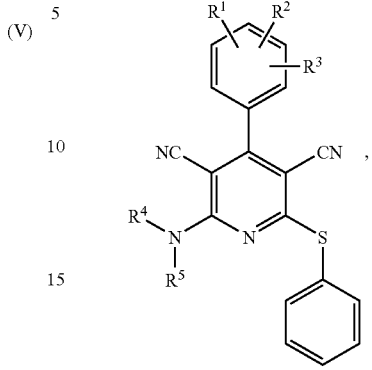

(VII)

in which
R$^1$, R$^2$, R$^3$, R$^4$ and R$^5$ are as defined above,
and finally converting them with sodium sulfide into compounds of the formula (II).

The preparation of compounds of the formula (II) can be illustrated in an exemplary manner by the formula scheme below:

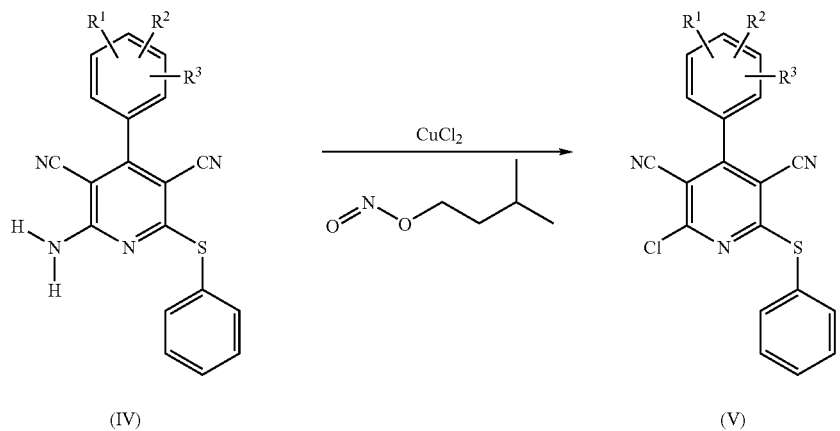

(IV) (V)

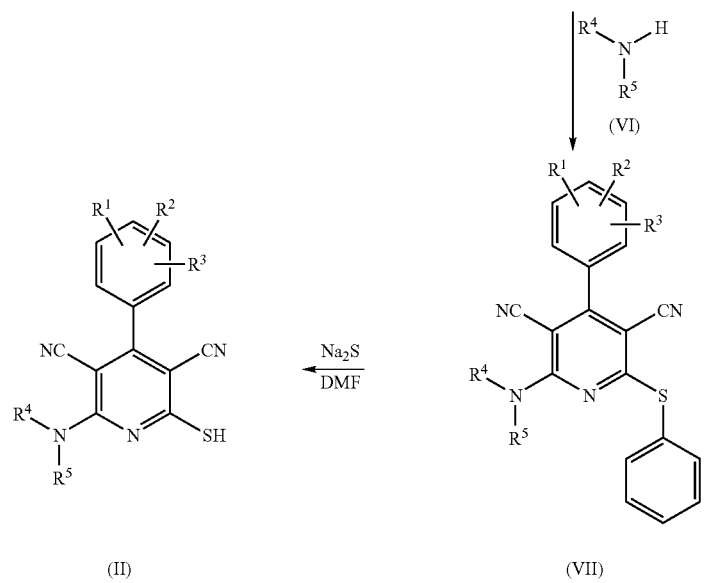

(II) (VII)

The process step (IV)→(V) is generally carried out in a molar ratio of from 2 to 12 mol of copper(II) chloride and from 2 to 12 mol of isoamyl nitrite per mole of (IV).

Suitable solvents for this process step are all organic solvents which are inert under the reaction conditions. These include, acyclic and cyclic ethers, such as diethyl ether and tetrahydrofuran, esters, such as ethyl acetate or butyl acetate, hydrocarbons, such as benzene, xylene, toluene, hexane or cyclohexane, chlorinated hydrocarbons, such as dichloromethane, chlorobenzene or dichloroethane, or other solvents, such as dimethylformamide, acetonitrile or pyridine. It is also possible to use mixtures of the solvents mentioned above. Preferred solvents are acetonitrile and dimethylformamide.

The reaction is generally carried out in a temperature range of from −78° C. to +180° C., preferably in a range of from +20° C. to +100° C., in particular at from +20 to +60° C.

The reaction can be carried out at atmospheric, elevated or reduced pressure (for example in the range from 0.5 to 5 bar). In general, the reaction is carried out at atmospheric pressure.

The process step (V)+(VI)→(VII) is generally carried out in a molar ratio of from 1 to 8 mol of (VI) per mole of (V).

Suitable solvents are all organic solvents which are inert under the reaction conditions. These include, alcohols, such as methanol, ethanol and isopropanol, ketones, such as acetone and methyl ethyl ketone, acyclic and cyclic ethers, such as diethyl ether and tetrahydrofuran, esters, such as ethyl acetate or butyl acetate, hydrocarbons, such as benzene, xylene, toluene, hexane or cyclohexane, chlorinated hydrocarbons, such as dichloromethane, chlorobenzene or dichloroethane, or other solvents, such as dimethylformamide, acetonitrile, pyridine or dimethyl sulfoxide (DMSO). Water is another suitable solvent. It is also possible to use mixtures of the solvents mentioned above. The preferred solvent is dimethylformamide.

The reaction is generally carried out in a temperature range of from −78° C. to +180° C., preferably in a range of from +20° C. to +160° C., in particular at from +20 to +40° C.

The reaction can be carried out at atmospheric, elevated or reduced pressure (for example in the range from 0.5 to 5 bar). In general, the reaction is carried out at atmospheric pressure.

The process step (VII)→(II) is generally carried out in a molar ratio of from 1 to 8 [lacuna] of sodium sulfide per mole of (VII).

Suitable solvents are all organic solvents which are inert under the reaction conditions. These include, alcohols, such as methanol, ethanol and isopropanol, ketones, such as acetone and methyl ethyl ketone, acyclic and cyclic ethers, such as diethyl ether and tetrahydrofuran, esters, such as ethyl acetate or butyl acetate, hydrocarbons, such as benzene, xylene, toluene, hexane or cyclohexane, chlorinated hydrocarbons, such as dichloromethane, chlorobenzene or dichloroethane, or other solvents, such as dimethylformamide, acetonitrile, pyridine or dimethyl sulfoxide (DMSO). It is also possible to use mixtures of the solvents mentioned above. The preferred solvent is dimethylformamide.

The reaction is generally carried out in a temperature range of from −78° C. to +180° C., preferably in a range of from +20° C. to +160° C., in particular at from +40 to +100° C.

The reaction can be carried out at atmospheric, elevated or reduced pressure (for example in the range from 0.5 to 5 bar). In general, the reaction is carried out at atmospheric pressure.

The compounds of the formula (IV) are known to the person skilled in the art or can be prepared by customary methods known from the literature. Reference may be made, in particular, to the following publications, whose respective content is incorporated herein by way of reference:

Kambe et al., Synthesis 1981, pages 531-533
Elnagdi et al., Z. Naturforsch. 47b, pages 572-578, (1991)

The compounds of the formulae (III) and (VI) are either commercially available, known to the person skilled in the art or preparable by customary methods.

Surprisingly, the compounds of the formula (I) have an unforeseeable useful pharmacological activity spectrum and are therefore suitable in particular for the prophylaxis and/or treatment of disorders.

The compounds of the formula (I) are suitable for the prophylaxis and/or treatment of a number of disorders, such as, for example, in particular disorders of the cardiovascular system (cardiovascular disorders).

In the context of the present invention, cardiovascular disorders are to be understood as meaning, in particular, for example the following disorders: coronary heart disease, hypertension (high blood pressure), restenosis, such as, for example, after balloon dilation of peripheral blood vessels, arteriosclerosis, tachycardia, arrhythmias, peripheral vascular disorders and cardiovascular disorders, stable and unstable angina pectoris and atrial fibrillation.

The compounds of the formula (I) are furthermore also particularly suitable, for example, for reducing the size of the myocardial area affected by an infarct.

The compounds of the formula (I) are furthermore particularly suitable, for example, for the prophylaxis and/or treatment of thromboembolic disorders and ischemias, such as myocardial infarction, stroke and transitory ischemic attacks.

Further areas of indication for which the compounds of the formula (I) are suitable are, for example, in particular the prophylaxis and/or treatment of disorders of the urogenital system, such as, for example, an irritable bladder, erectile dysfunction and female sexual dysfunction, and cancer, but additionally also the prophylaxis and/or treatment of inflammatory disorders, such as, for example, asthma and inflammatory dermatoses, of neuroinflammatory disorders of the central nervous system, such as, for example, disorders after stroke, Alzheimer's disease, and furthermore also neurodegenerative disorders, such as Parkinson's disease, and also pain.

A further area of indication is, for example, in particular the prophylaxis and/or treatment of disorders of the respiratory tract, such as, for example, asthma, chronic bronchitis, pulmonary emphysema, bronchiectases, cystic fibrosis (mucoviscidosis) and pulmonary hypertension.

The compounds of the formula (I) are furthermore also suitable, for example, in particular for the prophylaxis and/or treatment of liver fibrosis and liver cirrhosis.

Finally, the compounds of the formula (I) are in particular also suitable, for example, for the prophylaxis and/or treatment of diabetes, in particular diabetes mellitus.

The present invention also relates to the use of the substances of the formula (I) for preparing medicaments and pharmaceutical compositions for the prophylaxis and/or treatment of the clinical pictures mentioned above.

The present invention furthermore relates to a method for the prophylaxis and/or treatment of the clinical pictures mentioned above using the substances of the formula (I).

The pharmaceutical activity of the compounds of the formula (I) mentioned above can be explained by their activity as selective ligands on individual subtypes or a plurality of subtypes of the adenosine receptors, in particular as selective ligands on adenosine A1, adenosine A2a and/or adenosine A2b receptors, preferably as selective ligands on adenosine A1 and/or adenosine A2b receptors.

In the context of the present invention, adenosine receptor ligands are referred to as being "selective" if, firstly, they are clearly active on one or more adenosine receptor subtypes and, secondly, the activity that can be observed on one or more other adenosine receptor subtypes is considerably weaker, if present at all, where, with respect to the test methods for selectivity of action, reference is made to the test methods described in Section A. II.

One advantage of the compounds of the formula (I) according to the invention is that they are more selective than adenosine receptor ligands of the prior art.

In particular, compounds of the formula (I) in which $R^6$ represents an alkyl radical which is substituted by phenyl, alkoxy or hydroxyl generally act selectively on adenosine A1 receptors.

In particular, compounds of the formula (I) in which $R^6$ represents an alkyl radical which is substituted by —$CONH_2$, imidazole or pyridine generally act selectively on adenosine A1 and adenosine A2b receptors.

The receptor selectivity can be determined by biochemical measurement of the intracellular messenger cAMP in cells which specifically only express one subtype of the adenosine receptors. Here, what is observed, in the case of A2a and A2b agonists (coupling preferably via Gs proteins) and in the case of A2a and A2b antagonists, is an increase of the intracellular cAMP concentration and a decrease of the intracellular cAMP concentration, respectively, following prestimulation with adenosine or adenosine-like substances (see the publications B. Kull, G. Arslan, C. Nilsson, C. Owman, A. Lorenzen, U. Schwabe, B. B. Fredholm, "Differences in the order of potency for agonists but not antagonists at human and rat adenosine A2A receptors", Biochem. Pharmacol., 57 (1999) pages 65-75; and S. P. Alexander, J. Cooper, J. Shine, S. J. Hill, "Characterization of the human brain putative A2B adenosine receptor expressed in Chinese hamster ovary (CHO.A2B4) cells", Br. J. Pharmacol., 119 (1996) pages 1286-90, the respective content of which is expressly incorporated herein by way of reference). Correspondingly, A1 agonists (coupling preferably via Gi proteins) and A1 antagonists result in a decrease and increase, respectively, of the cAMP concentration.

Thus, compounds of the formula (I) which bind selectively to adenosine A1 receptors are preferably suitable for myocard protection and for the prophylaxis and/or treatment of tachycardia, atrial arrhythmias, cardiac insufficiency, myocardial infarction, acute kidney failure, diabetes, pain and for wound healing.

Compounds of the formula (I) which bind selectively to adenosine A2a receptors are preferably suitable for the prophylaxis and/or treatment of thromboembolic disorders, of neurodegenerative disorders such as Parkinson's disease and for wound healing.

Compounds of the formula (I) which bind selectively to adenosine A2b-receptors are preferably suitable for the prophylaxis and/or therapy of liver fibrosis, of myocardial infarction, of neuroinflammatory disorders, of Alzheimer's disease, of urogenital incontinence and of disorders of the respiratory tract, such as, for example, asthma and chronic bronchitis.

The present invention also provides medicaments and pharmaceutical compositions comprising at least one compound of the formula (I), preferably together with one or more pharmacologically acceptable auxiliaries or carriers, and their use for the abovementioned purposes.

Suitable for administering the compounds of the formula (I) are all customary administration forms, i.e. oral, parenteral, inhalative, nasal, sublingual, rectal, local, such as, for example, in the case of implants or stents, or external, such as, for example, transdermal. In the case of parenteral administration, particular mention may be made of intravenous, intramuscular and subcutaneous administration, for example as a subcutaneous depot. Particular preference is given to oral administration.

Here, the active compounds can be administered on their own or in the form of preparations. Suitable preparations for oral administration are inter alia tablets, capsules, pellets, sugar-coated tablets, pills, granules, solid and liquid aerosols, syrups, emulsions, suspensions and solutions. Here, the active compound has to be present in such a quantity that a therapeutic effect is obtained. In general, the active compound can be present in a concentration of from 0.1 to 100% by weight, in particular from 0.5 to 90% by weight, preferably from 5 to 80% by weight, i.e. the active compound should be present in quantities sufficient to achieve the dosage range mentioned.

To this end, the active compounds can be converted in a manner known per se to the customary preparations. This is achieved using inert nontoxic pharmaceutically suitable carriers, auxiliaries, solvents, vehicles, emulsifiers and/or dispersants.

Auxiliaries which may be mentioned are, for example: water, nontoxic organic solvents, such as, for example, paraffins, vegetable oils (for example sesame oil), alcohols (for example ethanol, glycerol), glycols (for example polyethylene glycol), solid carriers, such as natural or synthetic ground minerals (for example talc or silicates), sugars (for example lactose), emulsifiers, dispersants (for example polyvinylpyrrolidone) and glidants (for example magnesium sulfate).

In the case of oral administration, tablets may, of course, also contain additives such as sodium citrate, together with adjuvants such as starch, gelatin and the like. Aqueous preparations for oral administration may furthermore be admixed with flavor enhancers or colorants.

In general, it has been found to be advantageous to administer, in the case of parenteral administration, quantities of from about 0.1 to about 10 000 µg/kg, preferably from about 1 to about 1000 µg/kg, in particular from about 1 µg/kg to about 100 µg/kg, of body weight, to obtain effective results. In the case of oral administration, the quantity is from about 0.1 to about 10 mg/kg, preferably from about 0.5 to about 5 mg/kg, in particular from about 1 to about 4 mg/kg, of body weight.

In spite of this, it may still be necessary, depending on body weight, administration route, individual response to the active compound, the type of preparation and the time or interval at which administration takes place, to deviate from the quantities mentioned.

The present invention is illustrated by the following examples, although these do not restrict the invention in any way.

A. Assessing Physiological Activity

I. Detecting the Cardiovascular Effect

Langendorff Heart of the Rat:

After the thorax has been opened, the heart is removed from anesthetized rats and introduced into a conventional Langendorff apparatus. The coronary arteries are perfused at constant volume (10 ml/min), and the resulting perfusion pressure is recorded by way of an appropriate pressure sensor. In this set-up, a decrease in the perfusion pressure corresponds to a relaxation of the coronary arteries. At the same time, the pressure which the heart develops during each contraction is measured by way of a balloon, which has been introduced into the left ventricle, and a second pressure sensor. The frequency of the heart, which is beating in isolation, is calculated from the number of contractions per time unit.

II. Assessing the Receptor Selectivity a) Adenosine A1, A2a, A2b and A3 Receptor Selectivity Cells of the CHO (Chinese Hamster Ovary) permanent line are transfected stably with the cDNA for the adenosine receptor subtypes A1, A2a, A2b and A3. The binding of the substances to the A2a or A2b receptor subtypes is determined by measuring the intracellular cAMP content in these cells using a conventional radioimmunological assay (cAMP RIA).

When the substances act as agonists, the binding of the substances is expressed as an increase in the intracellular content of cAMP. The adenosine-analogous compound NECA (5-N-ethylcarboxamido-adenosine), which binds to all adenosine receptor subtypes with high affinity but not selectively and possesses an agonistic effect, is used as the reference compound in these experiments (Klotz, K. N., Hessling, J., Hegler, J., Owman, C., Kull, B., Fredholm, B. B., Lohse, M. J., Comparative pharmacology of human adenosine receptor subtypes—characterization of stably transfected receptors in CHO cells, Naunyn Schmiedebergs Arch Pharmacol, 357 (1998), 1-9).

The adenosine receptors A1 and A3 are coupled to a Gi protein, i.e. stimulation of these receptors leads to inhibition of the adenylate cyclase and consequently to a lowering of the intracellular cAMP level. In order to identify A1/A3 receptor agonists, the adenylate cyclase is stimulated with forskolin. However, an additional stimulation of the A1/A3 receptors inhibits the adenylate cyclase, which means that A1/A3 receptor agonists can be detected by a comparatively low content of cAMP in the cell.

In order to detect an antagonistic effect on adenosine receptors, the recombinant cells which are transfected with the corresponding receptor are prestimulated with NECA and the effect of the substances on reducing the intracellular content of cAMP occasioned by this prestimulation is investigated. XAC (xanthine amine congener), which binds to all adenosine receptor subtypes with high affinity but not selectively and possesses an antagonistic effect, is used as the reference compound in these experiments (Müller, C. E., Stein, B., Adenosine receptor antagonists: structures and potential therapeutic applications, Current Pharmaceutical Design, 2 (1996) 501-530).

b) Adenosine A1, A2a, A2b Receptor Selectivity

Cells of the CHO (Chinese Hamster Ovary) permanent line are transfected stably with the cDNA for the adenosine receptor subtypes A1, A2a and A2b. The adenosine A1 receptors are coupled to the adenylate cyclase by way of Gi proteins, while the adenosine A2a and A2b receptors are coupled by way of Gs proteins. In correspondence with this, the formation of cAMP in the cell is inhibited or stimulated, respectively. After that, expression of the luciferase is modulated by way of a cAMP-dependent promoter. The luciferase test is optimized, with the aim of high sensitivity and reproducibility, low variance and good suitability for implementation on a robot system, by varying several test parameters, such as cell density, duration of the growth phase and the test incubation, forskolin concentration and medium composition. The following test protocol is used for pharmacologically characterizing the cells and for the robot-assisted substance test screening:

The stock cultures is grown, at 37° C. and under 5% $CO_2$, in DMEM/F12 medium containing 10% FCS (fetal calf serum) and in each case split 1:10 after 2-3 days. The test cultures are seeded in 384-well plates at the rate of from 1 000 to 3 000 cells per well and grown at 37° C. for approx. 48 hours. The medium is then replaced with a physiological sodium chloride solution (130 mM NaCl, 5 mM KCl, 2 mM $CaCl_2$, 20 mM HEPES, 1 mM $MgCl_2.6H_2O$, 5 mM $NaHCO_3$, pH 7.4). The substances, which are dissolved in DMSO, are diluted 1:10 three times with this physiological sodium chloride solution and pipetted into the test cultures (maximum final concentration of DMSO in the test mixture: 0.5%). In this way, final substance concentrations of, for example, from 5 μM to 5 nM are obtained. 10 minutes later, forskolin is added to the A1 cells and all the cultures are subsequently incubated at 37° C. for 4 hours. After that, 35 μl of a solution which is composed of 50% lysis reagent (30 mM disodium hydrogenphosphate, 10% glycerol, 3% TritonX100, 25 mM Tris HCl, 2 mM dithiothreitol (DTT), pH 7.8) and 50% luciferase substrate solution (2.5 mM ATP, 0.5 mM luciferin, 0.1 mM coenzyme A, 10 mM tricine, 1.35 mM $MgSO_4$, 15 mM DTT, pH 7.8) are added to the test cultures, the plates are shaken for approx. 1 minute and the luciferase activity is measured using a camera system.

B. SYNTHESIS EXAMPLES

Example 1

Step 1

2-Chloro-4-phenyl-6-(phenylsulfanyl)-3,5-pyridinedicarbonitrile

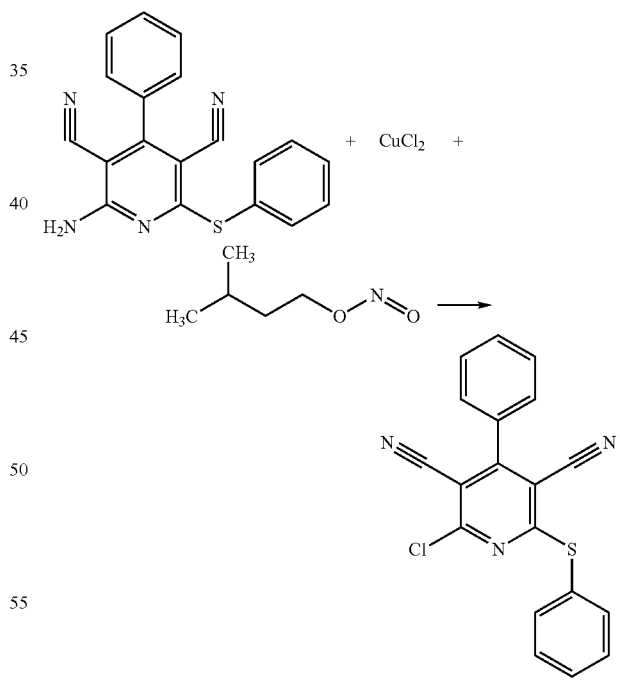

Under argon, 24.5 g (182 mmol) of anhydrous copper(II) chloride are suspended in 180 ml of acetonitrile, and 21.4 g (182 mmol) of isopentyl nitrite are then added dropwise. After 20 minutes of stirring at room temperature, 10 g (30.5 mmol) of 2-amino-4-phenyl-6-(phenylsulfanyl)-3,5-pyridinedicarbonitrile [Kambe et al., Synthesis, 531-533 (1981)] are added. The mixture is stirred at room temperature over the weekend. For work-up, 150 ml of 1 N hydrochloric acid are added to the mixture, the mixture is extracted 4× with dichloromethane and the organic phase is washed once with saturated sodium chloride solution, dried over magnesium sulfate and concentrated under reduced pressure. The residue is triturated with a little ethyl acetate and allowed to stand in a fridge for one hour. The crystals are filtered off with suction and washed with a little cold ethyl acetate and diethyl ether.

Yield: 7.26 g (68.5% of theory) of product

Mass spectrum: molar mass required: 347, found [M+H]$^+$=348

Step 2

2-Dimethylamino-4-phenyl-6-phenylsulfanyl-3,5-pyridinedicarbonitrile

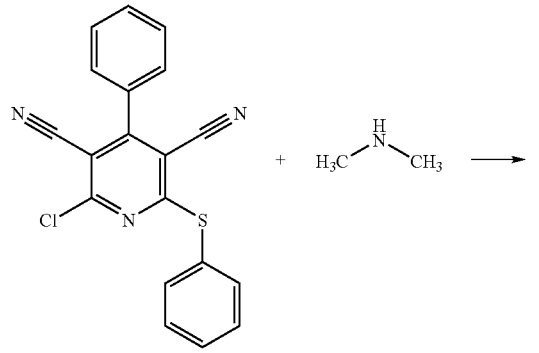

Under argon, 835 mg (2.4 mmol) of 2-chloro-4-phenyl-6-phenylsulfanyl-3,5-pyridinedicarbonitrile (step 1) are dissolved in 4 ml of absolute dimethylformamide (DMF), 0.330 ml of a 2 molar solution of dimethylamine in tetrahydrofuran (THF) is added and the reaction mixture is stirred at room temperature for 2 hours and then purified by preparative HPLC.

Mobile phase: acetonitrile/water (+0.3% trifluoroacetic acid (TFA)), 10/90 to 90/10; 45 ml/min;

column: Kromasil 100 C18, 10 µm, 75×30 mm

Detection: 220 nm.

The product fraction is concentrated by evaporation and dried under reduced pressure overnight.

Yield: 280 mg (32.7% of theory) of product

Mass spectrum: molar mass required: 356, found [M+H]$^+$=357

Step 3

2-Dimethylamino-4-phenyl-6-sulfanyl-3,5-pyridinedicarbonitrile

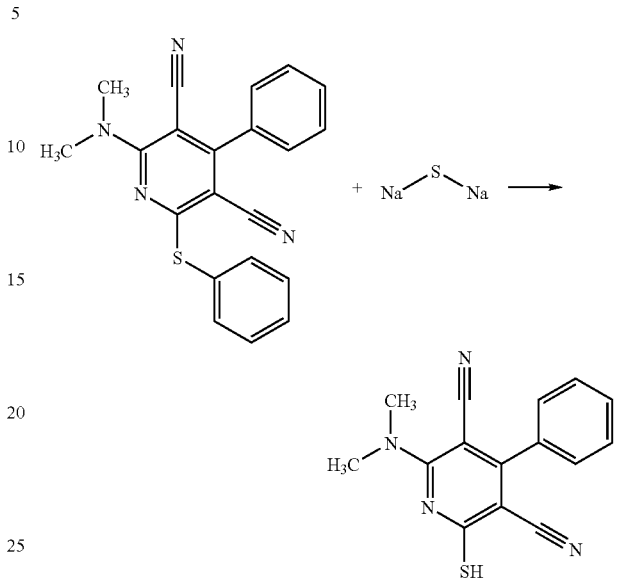

Under argon, 280 mg (0.79 mmol) of 2-dimethylamino-4-phenyl-6-phenylsulfanyl-3,5-pyridinedicarbonitrile (step 2) are dissolved in 3 ml of abs. dimethylformamide (DMF), and 204 mg (2.6 mmol) of sodium sulfide are added. The reaction mixture is stirred at 80° C. for 2 hours. 6 ml of 1 N hydrochloric acid are added to the mixture and the resulting yellow crystals are filtered off with suction, washed with water and petroleum ether/diethyl ether 1/1 and dried under reduced pressure overnight.

Yield: 117 mg (53% of theory) of product

Mass spectrum: molar mass required: 280, found [M+H]$^+$=281

Step 4

2-Dimethylamino-6-[(2-hydroxyethyl)sulfanyl]-4-phenyl-3,5-pyridinedicarbonitrile

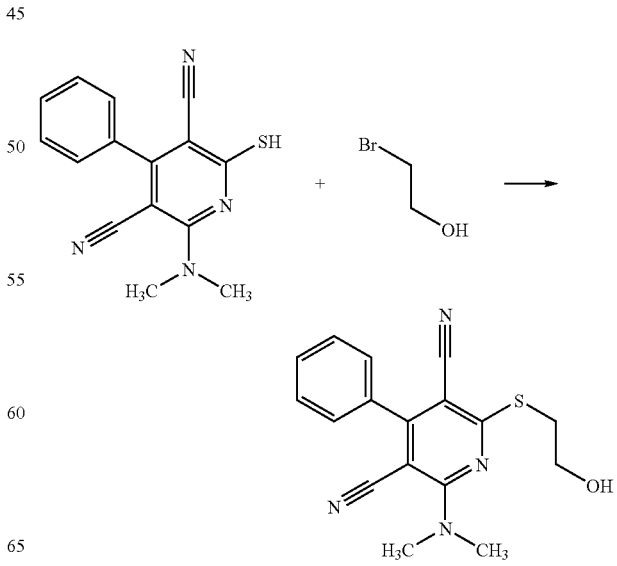

28 mg (0.1 mmol) of 2-dimethylamino-4-phenyl-6-sulfanyl-3,5-pyridinedicarbonitrile (step 3) are, together with 19 mg (0.15 mmol) of 2-bromoethanol and 34 mg (0.4 mmol) of sodium bicarbonate, shaken in 0.6 ml of dimethylformamide (DMF) for about 16 hours. After filtration, the reaction solution is purified by preparative HPLC.

Column: Grom-Sil 120 ODS-4HE, 5 μm;

Mobile phase: acetonitrile/water+0.3% trifluoroacetic acid (TFA) 10/90 to 90/10; 25 ml/min;

Detection: 254 nm.

The product fraction is concentrated by evaporation under reduced pressure.

Yield: 23 mg (71% of theory) of product

Mass spectrum: molar mass required: 324, found [M+H]$^+$=325

$^1$H-NMR spectrum [DMSO-d$_6$]: δ=3.35 [6H] s; 3.35 [2H] tr; 3.7 [2H] quartet; 5.0 [1H] tr; 7.55 [5H] m.

The compounds listed in the table below (examples 2 to 90) are prepared analogously to the procedures of example 1 given above. The identity and purity of the compounds is examined by LC-MS.

| Ex. No. | Target structure | Molar mass required | Found [M + H]$^+$ | Yield (% of theory) | NMR data |
|---------|------------------|---------------------|-------------------|---------------------|----------|
| 2 | | 324 | 325 | 54 | |
| 3 | | 370 | 371 | 44 | |
| 4 | | 354 | 355 | 66 | |
| 5 | | 405 | 406 | 54 | |

-continued

| Ex. No. | Target structure | Molar mass required | Found [M + H]+ | Yield (% of theory) | NMR data |
|---|---|---|---|---|---|
| 6 | | 354 | 355 | 69 | |
| 7 | | 401 | 402 | 52 | |
| 8 | | 435 | 436 | 48 | |
| 9 | | 310 | 311 | 55 | $^1$H-NMR spectrum [DMSO-$d_6$]: δ = 3.05[3H] d; 3.35[2H] tr; 3.7[2H] quartet; 5.0[1H] tr; 7.55[5H] m; 8.15[1H] broad. |
| 10 | | 356 | 357 | 39 | |

-continued

| Ex. No. | Target structure | Molar mass required | Found [M + H]+ | Yield (% of theory) | NMR data |
|---|---|---|---|---|---|
| 11 | | 340 | 341 | 49 | |
| 12 | | 391 | 392 | 37 | |
| 13 | | 340 | 341 | 76 | |
| 14 | | 386 | 387 | 57 | $^1$H-NMR spectrum [DMSO-d$_6$]: δ = 3.6[4H] m; 4.55[2H] s; 4.8[1H] tr; 7.25-7.6[10H] m; 8.0[1H] broad |

-continued

| Ex. No. | Target structure | Molar mass required | Found [M + H]+ | Yield (% of theory) | NMR data |
|---|---|---|---|---|---|
| 15 | | 421 | 422 | 58 | |
| 16 | | 367 | 368 | 50 | |
| 17 | | 350 | 351 | 40 | |
| 18 | | 363 | 364 | 22 | |

-continued
| Ex. No. | Target structure | Molar mass required | Found [M + H]+ | Yield (% of theory) | NMR data |
|---|---|---|---|---|---|
| 19 | 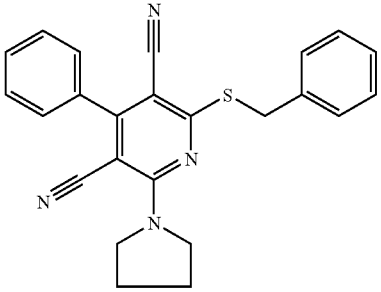 | 397 | 398 | 36 | |
| 20 | 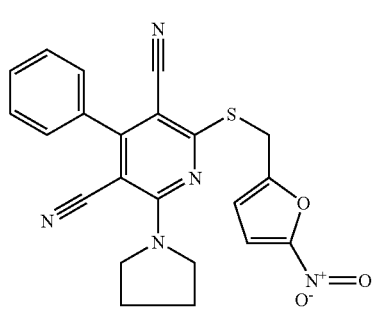 | 431 | 432 | 39 | |
| 21 | 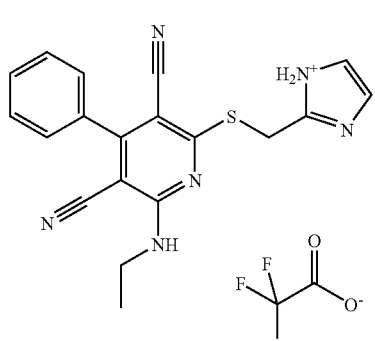 | 360 | 361 | 63 | |
| 22 | 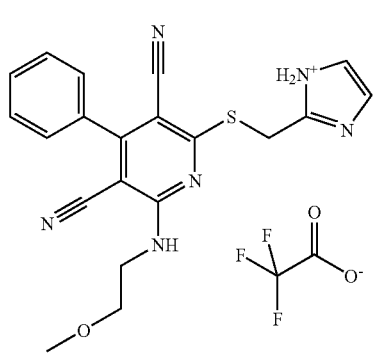 | 390 | 391 | 60 | |

-continued

| Ex. No. | Target structure | Molar mass required | Found [M + H]+ | Yield (% of theory) | NMR data |
|---|---|---|---|---|---|
| 23 | | 346 | 347 | 36 | |
| 24 | | 387 | 388 | 31 | |
| 25 | | 393 | 394 | 38 | |
| 26 | | 406 | 407 | 14 | |

-continued

| Ex. No. | Target structure | Molar mass required | Found [M + H]+ | Yield (% of theory) | NMR data |
|---|---|---|---|---|---|
| 27 | | 441 | 442 | 72 | |
| 28 | | 470 | 471 | 44 | |
| 29 | | 471 | 472 | 61 | |
| 30 | | 444 | 445 | 73 | |

-continued

| Ex. No. | Target structure | Molar mass required | Found [M + H]+ | Yield (% of theory) | NMR data |
|---|---|---|---|---|---|
| 31 | | 445 | 446 | 44 | |
| 32 | | 411 | 412 | 42 | |
| 33 | | 458 | 459 | 56 | |
| 34 | | 459 | 460 | 63 | |

-continued

| Ex. No. | Target structure | Molar mass required | Found [M + H]+ | Yield (% of theory) | NMR data |
|---|---|---|---|---|---|
| 35 | | 411 | 412 | 28 | |
| 36 | | 458 | 459 | 72 | |
| 37 | | 459 | 460 | 55 | |
| 38 | | 484 | 485 | 73 | |

-continued

| Ex. No. | Target structure | Molar mass required | Found [M + H]+ | Yield (% of theory) | NMR data |
|---|---|---|---|---|---|
| 39 | | 485 | 486 | 53 | |
| 40 | | 457 | 458 | 69 | |
| 41 | | 455 | 456 | 51 | |
| 42 | | 381 | 382 | 41 | |

-continued

| Ex. No. | Target structure | Molar mass required | Found [M + H]+ | Yield (% of theory) | NMR data |
|---|---|---|---|---|---|
| 43 | | 428 | 429 | 40 | |
| 44 | | 429 | 430 | 52 | |
| 45 | | 395 | 396 | 46 | |
| 46 | | 367 | 368 | 39 | |
| 47 | | 380 | 381 | 34 | |

-continued

| Ex. No. | Target structure | Molar mass required | Found [M + H]+ | Yield (% of theory) | NMR data |
|---|---|---|---|---|---|
| 48 | | 414 | 415 | 39 | |
| 49 | | 414 | 415 | 58 | |
| 50 | | 381 | 382 | 38 | |
| 51 | | 439 | 440 | 56 | |

-continued

| Ex. No. | Target structure | Molar mass required | Found [M + H]+ | Yield (% of theory) | NMR data |
|---|---|---|---|---|---|
| 52 | | 485 | 486 | 53 | |
| 53 | | 455 | 456 | 60 | |
| 54 | | 337 | 338 | 71 | |
| 55 | | 351 | 352 | 51 | |

-continued
| Ex. No. | Target structure | Molar mass required | Found [M + H]+ | Yield (% of theory) | NMR data |
|---|---|---|---|---|---|
| 56 | 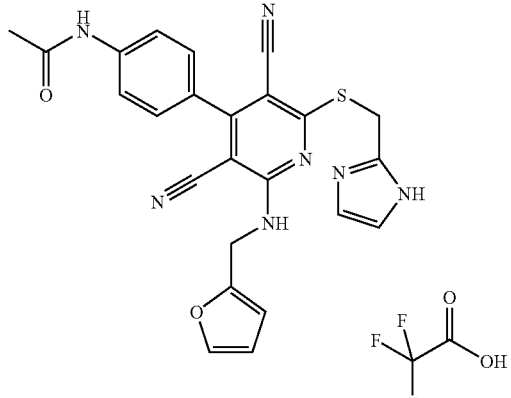 | 470 | 471 | 51 | |
| 57 | 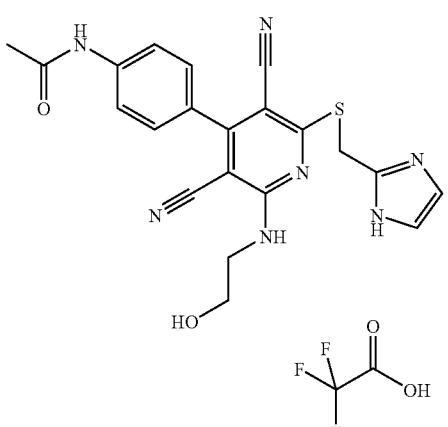 | 434 | 435 | 41 | |
| 58 | 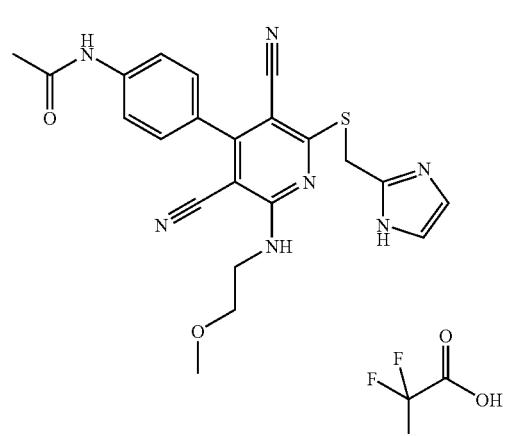 | 448 | 449 | 47 | |

-continued

| Ex. No. | Target structure | Molar mass required | Found [M + H]+ | Yield (% of theory) | NMR data |
|---|---|---|---|---|---|
| 59 | | 488 | 489 | 63 | |
| 60 | | 484 | 485 | 48 | |
| 61 | | 448 | 449 | 31 | |

-continued

| Ex. No. | Target structure | Molar mass required | Found [M + H]+ | Yield (% of theory) | NMR data |
|---|---|---|---|---|---|
| 62 | | 474 | 475 | 45 | |
| 63 | | 432 | 433 | 68 | |
| 64 | | 446 | 447 | 51 | |

-continued

| Ex. No. | Target structure | Molar mass required | Found [M + H]+ | Yield (% of theory) | NMR data |
|---|---|---|---|---|---|
| 65 | | 444 | 445 | 62 | |
| 66 | | 481 | 482 | 38 | |
| 67 | | 418 | 419 | 57 | |

| Ex. No. | Target structure | Molar mass required | Found [M + H]+ | Yield (% of theory) | NMR data |
|---|---|---|---|---|---|
| 68 | | 417 | 418 | 65 | ¹H-NMR spectrum [DMSO-d₆]: δ = 3.0[3H] d; 3.75[2H] quartet; 4.05[2H] tr; 4.6[2H] s; 4.95[1H] tr; 7.05-7.5[3H] m; 8.15[1H] quartet |
| 69 | | 431 | 432 | 33 | |
| 70 | | 447 | 448 | 6 | ¹H-NMR spectrum [DMSO-d₆]: δ = 3.6[4H] m; 3.7[2H] quartet; 4.1[2H] tr; 4.5[2H] s; 4.8[1H] tr; 4.9[1H] tr; 7.05-7.5[3H] m; 7.95[1H] s broad |

-continued

| Ex. No. | Target structure | Molar mass required | Found [M + H]+ | Yield (% of theory) | NMR data |
|---|---|---|---|---|---|
| 71 | | 400 | 401 | 101 | |
| 72 | | 414 | 415 | 84 | |
| 73 | | 430 | 431 | 89 | |
| 74 | | 445 | 446 | 112 | |

-continued

| Ex. No. | Target structure | Molar mass required | Found [M + H]+ | Yield (% of theory) | NMR data |
|---|---|---|---|---|---|
| 75 | | 426 | 427 | 89 | |
| 76 | | 441 | 442 | 90 | |
| 77 | | 445 | 446 | 93 | |
| 78 | | 445 | 446 | 72 | |

-continued

| Ex. No. | Target structure | Molar mass required | Found [M + H]+ | Yield (% of theory) | NMR data |
|---|---|---|---|---|---|
| 79 | | 355 | 355 | 77 | ¹H-NMR spectrum [DMSO-d₆]: δ = 3.0[3H] d; 3.4[2H] tr; 3.7[2H] quartet; 5.05[1H] tr; 6.15[2H] s; 6.95-7.15[3H] m; 8.1[1H] s broad |
| 80 | | 368 | 369 | 82 | ¹H-NMR spectrum [DMSO-d₆]: δ = 1.2[3H] tr; 3.4[2H] tr; 3.5[2H] quintet; 3.65[2H] quartet; 5.05[1H] tr; 6.15[2H] s; 6.95-7.15[3H] m; 8.2[1H] tr |
| 81 | | 384 | 385 | 83 | |
| 82 | | 398 | 399 | 82 | |
| 83 | | 380 | 381 | 88 | ¹H-NMR spectrum [DMSO-d₆]: δ = 0.65-0.9[4H] m; 2.9[1H] m; 3.4[2H] tr; 3.7[2H] tr; 5.0[1H] s broad; 6.15[2H] s; 6.95-7.15[3H] m; 8.3[1H] s broad |

-continued

| Ex. No. | Target structure | Molar mass required | Found [M + H]+ | Yield (% of theory) | NMR data |
|---|---|---|---|---|---|
| 84 | | 401 | 402 | 74 | ¹H-NMR spectrum [DMSO-d₆]: δ = 2.95[3H] s; 4.2[2H] s; 6.1[2H] s; 6.95-7.15[3H] m; 7.3[1H] tr; 7.5[1H] d; 7.75[1H] tr; 8.1[1H] s; 8.5[1H] s |
| 85 | | 368 | 369 | 88 | |
| 86 | | 382 | 383 | 88 | |
| 87 | | 398 | 399 | 93 | |
| 88 | | 412 | 413 | 84 | |

| Ex. No. | Target structure | Molar mass required | Found [M + H]+ | Yield (% of theory) | NMR data |
|---|---|---|---|---|---|
| 89 | | 382 | 383 | 85 | |
| 90 | 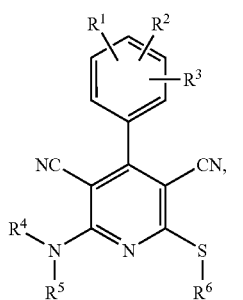 | 394 | 395 | 89 | |

The invention claimed is:

1. A compound of the formula (I)

(I)

in which

R$^1$, R$^2$ and R$^3$ independently of one another represent (C$_1$-C$_8$)-alkyl which may be substituted up to three times, independently of one another, by hydroxyl, (C$_1$-C$_4$)-alkoxy, (C$_3$-C$_7$)-cycloalkyl, (C$_2$-C$_4$)-alkenyl, (C$_2$-C$_4$)-alkynyl, halogen or (C$_6$-C$_{10}$)-aryloxy, (C$_6$-C$_{10}$)-aryl which may be substituted up to three times, independently of one another, by halogen, nitro, (C$_1$-C$_4$)-alkoxy, carboxyl, (C$_1$-C$_4$)-alkoxycarbonyl or mono- or di-(C$_1$-C$_4$)-alkylamino, (C$_1$-C$_8$)-alkoxy which may be substituted by hydroxyl, (C$_1$-C$_4$)-alkoxy, (C$_3$-C$_7$)-cycloalkyl, (C$_2$-C$_4$)-alkenyl, (C$_6$-C$_{10}$)-aryl, 5- or 6-membered heteroaryl having up to three heteroatoms from the group consisting of N, O and/or S, (C$_6$-C$_{10}$)-aryloxy, halogen, cyano, (C$_1$-C$_4$)-alkoxycarbonyl, amino or mono- or di-(C$_1$-C$_4$)-alkylamino, hydrogen, hydroxyl, halogen, nitro, cyano, or —NH—C(O)—R$^7$, in which R$^7$ represents (C$_1$-C$_8$)-alkyl which may be substituted by hydroxyl or (C$_1$-C$_4$)-alkoxy, (C$_3$-C$_7$)-cycloalkyl or (C$_6$-C$_{10}$)-aryl which may be substituted up to three times, independently of one another, by halogen, nitro, (C$_1$-C$_4$)-alkoxy, carboxyl, (C$_1$-C$_4$)-alkoxycarbonyl or mono- or di-(C$_1$-C$_4$)-alkylamino, or R$^1$ and R$^2$ are attached to adjacent phenyl ring atoms and, together with the two ring carbon atoms, form a 5- to 7-membered saturated or partially unsaturated heterocycle having one or two heteroatoms from the group consisting of N, O and/or S which may be substituted by (C$_1$-C$_4$)-alkyl or oxo, R$^4$ represents (C$_1$-C$_8$)-alkyl which may be substituted by hydroxyl, —NH—CO—R$^8$, (C$_1$-C$_4$)-alkoxy, (C$_3$-C$_7$)-cycloalkyl, (C$_6$-C$_{10}$)-aryl, 5- or 6-membered saturated or partially unsaturated heterocyclyl having up to three heteroatoms from the group consisting of N, O and/or S or 5- or 6-membered heteroaryl having up to three heteroatoms from the group consisting of N, O and/or S, or (C$_3$-C$_7$)-cycloalkyl which may be substituted by hydroxyl or (C$_1$-C$_8$)-alkyl, in which R$^8$ represents (C$_1$-C$_8$)-alkyl which may be substituted by hydroxyl or (C$_1$-C$_4$)-alkoxy, (C$_3$-C$_7$)-cycloalkyl or (C$_6$-C$_{10}$)-aryl which may be substituted up to three times, independently of one another, by halogen, nitro, (C$_1$-C$_4$)-alkoxy, carboxyl, (C$_1$-C$_4$)-alkoxycarbonyl or mono- or di-(C$_1$-C$_4$)-alkylamino, $R^5$ represents hydrogen or $(C_1-C_4)$-alkyl which may be substituted by hydroxyl, $(C_1-C_4)$-alkoxy or $(C_3-C_7)$-cycloalkyl, or $R^4$ and $R^5$ together with the nitrogen atom to which they are attached form a 5- to 7-membered saturated or partially unsaturated heterocycle which may contain one or two further heteroatoms from the group consisting of N, O and/or S in the ring and which may be mono- to trisubstituted, independently of one another, by oxo, fluorine, chlorine, bromine, hydroxyl, $(C_1-C_6)$-alkyl or $(C_1-C_6)$-alkoxy, and $R^6$ represents $(C_3-C_7)$-cycloalkyl or $(C_1-C_8)$-alkyl, where alkyl may be substituted up to three times, independently of one another, by $(C_3-C_7)$-cycloalkyl, hydroxyl, —CO—NH—$R^9$, $(C_1-C_4)$-alkoxy, $(C_2-C_4)$-alkenyl, $(C_6-C_{10})$-aryl or 5- to 10-membered heteroaryl having up to three heteroatoms from the group consisting of N, O and/or S, where aryl and heteroaryl for their part may be substituted by halogen, $(C_1-C_4)$-alkyl, $(C_1-C_4)$-alkoxy, amino, mono- or di-$(C_1-C_4)$-alkylamino, nitro, cyano or hydroxyl, and $R^9$ represents hydrogen, $(C_1-C_8)$-alkyl which may be substituted by hydroxyl or $(C_1-C_4)$-alkoxy, $(C_3-C_7)$-cycloalkyl or $(C_6-C_{10})$-aryl which may be substituted up to three times, independently of one another, by halogen, nitro, $(C_1-C_4)$-alkoxy, carboxyl, $(C_1-C_4)$-alkoxycarbonyl or mono- or di-$(C_1-C_4)$-alkylamino, or a salt, a hydrate, a hydrate of a salt or a solvate thereof.

2. A compound of the formula (I)

in which $R^1$, $R^2$ and $R^3$ independently of one another represent hydrogen, hydroxyl, $(C_1-C_4)$-alkyl, trifluoromethyl, trifluoromethoxy, fluorine, chlorine, $(C_1-C_4)$-alkoxy which may be substituted by hydroxyl, $(C_1-C_4)$-alkoxy, $(C_2-C_4)$-alkenyl or $(C_3-C_6)$-cycloalkyl, —NH—C(O)—CH$_3$ or —NH—C(O)—C$_2$H$_5$, or $R^1$ and $R^2$ are attached to adjacent phenyl ring atoms and represent a group —O—CH$_2$—O— or —O—CH$_2$—CH$_2$—O—, $R^4$ represents $(C_1-C_6)$-alkyl which may be substituted by hydroxyl, $(C_1-C_4)$-alkoxy, $(C_3-C_6)$-cycloalkyl, 13 NH—C(O)—CH$_3$, phenyl, furyl, pyridyl, imidazolyl, thienyl or hexahydropyranyl, or $(C_3-C_6)$-cycloalkyl, $R^5$ represents hydrogen or $(C_1-C_4)$-alkyl which may be substituted by hydroxyl, $(C_1-C_4)$-alkoxy or $(C_3-C_6)$-cycloalkyl, or $R^4$ and $R^5$ together with the nitrogen atom to which they are attached form a 5- to 7-membered saturated or partially unsaturated heterocycle which may contain a further heteroatom from the group consisting of N, O or S in the ring and which may be mono- to trisubstituted, independently of one another, by hydroxyl, $(C_1-C_4)$-alkyl or $(C_1-C_4)$-alkoxy, and $R^6$ represents $(C_3-C_6)$-cycloalkyl, $(C_1-C_6)$-alkyl which may be substituted up to two times, independently of one another, by $(C_3-C_6)$-cycloalkyl, —CO—NH—$R^9$, hydroxyl, $(C_1-C_4)$-alkoxy, $(C_2-C_4)$-alkenyl, phenyl or 5- or 6-membered heteroaryl having up to three heteroatoms from the group consisting of N, O and/or S, where phenyl and heteroaryl for their part may be substituted by halogen, $(C_1-C_4)$-alkyl, $(C_1-C_4)$-alkoxy, amino, mono- or di-$(C_1-C_4)$-alkylamino, nitro, cyano or hydroxyl, and $R^9$ represents hydrogen or $(C_1-C_4)$-alkyl, or a salt, a hydrate, a hydrate of a salt or a solvate thereof.

3. A compound of the formula (I)

in which $R^1$ and $R^2$ independently of one another represent hydrogen, methoxy, ethoxy, n-propoxy, isopropoxy, n-butoxy or —NH—C(O)—CH$_3$, where the alkoxy radicals for their part may be substituted by hydroxyl, methoxy, ethoxy, n-propoxy, isopropoxy, n-butoxy or cyclopropyl, or $R^1$ and $R^2$ are attached to adjacent phenyl ring atoms and represent a group —O—CH$_2$—O—, $R^3$ represents hydrogen, $R^4$ represents methyl, ethyl, n-propyl, isopropyl, where the alkyl radicals for their part may be substituted by hydroxyl, methoxy, ethoxy, n-propoxy, isopropoxy, n-butoxy, cyclopropyl, —NH—C(O)—CH$_3$, furyl, pyridyl, imidazolyl or hexahydropyranyl, or cyclopropyl, $R^5$ represents hydrogen or methyl, or $R^4$ and $R^5$ together with the nitrogen atom to which they are attached represent pyrrolidinyl, morpholinyl, piperidinyl or 4-hydroxypiperidinyl and $R^6$ represents methyl, ethyl or n-propyl, where the alkyl radicals for their part may be substituted up to two times, independently of one another, by hydroxyl, methoxy, ethoxy, n-propoxy, isopropoxy, n-butoxy, imidazolyl, nitrofuranyl, pyridyl, phenyl which for its part may in turn be substituted by cyano, nitro, methyl, ethyl, n-propyl, isopropyl, methoxy, ethoxy, n-propoxy, isopropoxy, n-butoxy or amino, —C(O)—NH$_2$ or —C(O)—NH—CH$_3$, or a salt, a hydrate, a hydrate of a salt or a solvate thereof.

4. A process for preparing compounds of the formula (I) as defined in claim 1, characterized in that a compound of the formula (II)

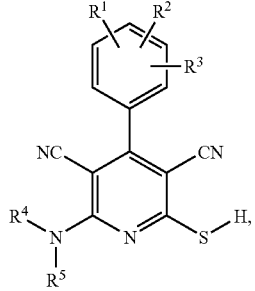

(II)

in which $R^1$, $R^2$, $R^3$, $R^4$ and $R^5$ are as defined in claim 1 is reacted with a compounds of the formula (III)

$R^6$—X  (III)

in which $R^6$ is as defined in claim 1 and X represents a leaving group.

5. A composition, comprising at least one compounds of the formula (I) as defined in claim 1 and at least one further auxiliary.

* * * * *